United States Patent [19]

Morris

[11] Patent Number: 5,674,746

[45] Date of Patent: *Oct. 7, 1997

[54] DNA PLASMIDS

[75] Inventor: Charles F. Morris, Newbury Park, Calif.

[73] Assignee: Amgen, Inc., Thousand Oaks, Calif.

[*] Notice: The term of this patent shall not extend beyond the expiration date of Pat. No. 4,710,473.

[21] Appl. No.: 243,604

[22] Filed: May 16, 1994

Related U.S. Application Data

[63] Continuation of Ser. No. 908,777, Jul. 1, 1992, abandoned, which is a continuation of Ser. No. 465,568, Jan. 16, 1990, abandoned, which is a continuation of Ser. No. 35,343, Apr. 7, 1987, abandoned, which is a continuation of Ser. No. 636,727, Aug. 6, 1984, Pat. No. 4,710,473, which is a continuation-in-part of Ser. No. 521,964, Aug. 10, 1983, abandoned.

[51] Int. Cl.$^6$ .................. C12N 15/73; C12N 15/70
[52] U.S. Cl. .................. 435/320.1; 435/172.3; 435/252.33; 935/29; 935/73
[58] Field of Search .................. 435/320.1, 172.3, 435/252.33; 935/29, 73

[56] References Cited

U.S. PATENT DOCUMENTS

| | | | |
|---|---|---|---|
| 4,374,927 | 2/1983 | Sninsky et al. | 435/69.1 |
| 4,487,835 | 12/1984 | Uhlin | 435/317.1 |

FOREIGN PATENT DOCUMENTS

| | | | |
|---|---|---|---|
| 0013830 | 8/1980 | European Pat. Off. | |
| 0060045 | 9/1982 | European Pat. Off. | |
| 1557774 | 12/1979 | United Kingdom | C12K 3/00 |
| 8304030 | 11/1983 | WIPO | |
| 8401171 | 3/1984 | WIPO | C12N 15/00 |
| 8401172 | 3/1984 | WIPO | C12N 15/00 |

OTHER PUBLICATIONS

Grindley et al., Abstracts of Second ASM Meeting on Extrachromosomal Elements, Jackson, WY Feb. 20-25, 1977.
Grindley et al. in Microbiology 1978, D. Schlessinger, ed., pp. 71-73 (1978).
Uhlin et al. Mol. Gen. Genet. 165, 167-179 (1978).
McKenney, et al., Gene Amplif. Anal., 2:383-415 (1981).
Som, et al., Plasmid, 5:150 et seq. (1981).
Stougaard, et al., Proc. Nat'l. Acad. Sci. USA, 78:6008-6012 (1981).
Shimatake et al, Nature 292:128 (1981).
Sninsky et al, Gene 16:275 (1981).
Stougaard et al, Molec. Gen. Genet. 181:116 (1981).
Uhlin, et al., *J. Bacteriol.*, 148:386-390 (1981).
Uhlin, et al., *Gene*, 6: 91-106 (1979).
Vieira, et al., *Gene*, 19: 259-268 (1982).
Yanofsky. Nature, 289: 751-758 (1981).
Adhya, et al., Ann. Rev. Biochem., 47: 967-996 (1978).
Bittner, et al., Gene, 15: 319-329 (1981).
Gentz, et al., Proc. Nat'l. Acad. Sci. USA, 78: 4936-4940 (Aug. 1981).
Hashimoto-Gotoh, et al., *Gene*, 16: 227-235 (1981).
Kollek, et al., *Mol. Gen. Genet.*, 162: 51-57 (1978).
Light, et al., E.M.B.O. Journal, 2:93-98 (1983).
Light, et al., J. Bacteriol., 151:1129-1135 (1982).
Meacock, et al., Cell, 20:529-542 (1980).
McKell, et al., (Abstract) p. 347, *J. Supramolecular Structure* Supp. No. 4, 9th Annual ICN-UCLA Symposium (1980).
Mickel, et al., *J. Bacteriol.*, 127: 644-655 (1976).
Molin, et al., *Mol. Gen. Genet.*, 18: 123-130 (1981).
Nordstrom, et al., *Plasmid*, 4: 215-227 (1980).
Remaut, et al., *Gene*, 22: 103-113 (1983).
Rosen et al., Mol. Gen. Genet., 179:527-537 (1980).
Rao et al, Gene vol. 3 pp. 247-263 (1978).
*Critical Synergy: The Biotechnology Industry and Intellectual Property Protection*, Presentations of the Intellectual Property Committee of the Biotechnology Industry Organization at the Oct. 17, 1994, Hearing of the U.S. Patent and Trademark Office, San Diego, CA. Biotechnology Industry Organization, 1625 K Street, NW, Suite 1100, Washington, DC, p. 100.
Maniatis, T., et al. Molecular Cloning (A Laboratory Manual), Cold Spring Harbor Laboratory, 73 and 100-102 (1982).
Ausubel, F. M. et al. Current Protocols in Molecular Biology, John Wiley and Sons, 1.8.1-1.8.5 (1989).
Derynck et al, Nature vol. 287 pp. 193-197.
Rao et al, Gene vol. 7 pp. 79-82 (1979).

*Primary Examiner*—James Martinell
*Attorney, Agent, or Firm*—Robert B. Winter; Ron K. Levy; Steven M. Odre

[57] ABSTRACT

Disclosed are novel circular DNA plasmids useful as vectors in recombinant methods to secure high levels of E.coli expression of exogenous genes. Plasmids of the invention comprise discrete DNA sequences operative to: (1) confer upon the plasmid the capacity for autonomous replication in a host cell; (2) control autonomous plasmid replication in relation to the temperature at which host cell cultures are maintained; (3) stabilize maintenance of the plasmid in host cell populations; (4) direct synthesis of a protein product indicative of plasmid maintenance in a host cell population; (5) provide, in series, a plurality of restriction endonuclease recognition sites, unique to the plasmid and facilitative of exogenous gene DNA sequence insertion; and (6) terminate mRNA transcription of adjacent DNA sequences and situated so as to terminate transcription of exogenous gene sequences inserted within the plasmid at said unique restriction endonuclease restriction sites. Plasmids preferably have a size of less than 5.0 kilobases (exclusive of any inserted exogenous gene) and optionally include a DNA sequence operative to provide a strong promoter of mRNA transcription functionally associated with a temperature sensitive repressor sequence. A presently preferred embodiment of novel plasmids of the invention is plasmid pCFM414 (A.T.C.C. No. 40076).

5 Claims, No Drawings

DNA PLASMIDS

This application is a continuation of application Ser. No. 07/908,777 filed Jul. 1, 1992, abandoned, which is a continuation of application Ser. No. 07/465,568, filed Jan. 16, 1990, now abandoned which is a continuation of application Ser. No. 07/035,343, filed Apr. 7, 1987, now abandoned, which is a continuation of application Ser. No. 636,731, filed Aug. 1, 1984, now U.S. Pat. No. 4,710,423, which is a continuation-in-part application of is application Ser. No. 521,964, filed Aug. 10, 1983, now abandoned.

BACKGROUND

The present invention relates generally to recombinant methods and materials for effecting the microbial product of useful polypeptides and more particularly to novel DNA plasmids useful in securing exceptionally high levels of expression of exogenous genes in *E.coli* host cells.

Numerous attempts have been made to optimize the extent to which exogenous genes are subject to expression in microbial host cell populations such as *E.coli*, *B.subtilis*, yeast and other microbial cell types. Among the initially more promising developments in the optimization of *E.coli* expression of "foreign" genes was isolation of the so-called "temperature dependent", "temperature sensitive", or "runaway mutant" forms of circular DNA plasmid. See, generally, Uhlin, et al., *Gene*, 6, pp. 91–106 (1979); Uhlin, et al., *J.Bacteriol.*, 148, pp. 386–390 (1981); Uhlin, et al., U.K. Patent Specification 1,557,774. These autonomously-replicating plasmids could generally be maintained in *E.coli* host cells in moderate copy numbers when the cells were cultured at a "permissive" temperature below 34° C., e.g., at about 30° C. Upon elevation of culture temperatures to a "non-permissive" level of 37° C. and above, inherent controls on autonomous replication of the plasmid within the host were lost and replication of the plasmid was said to "run away" until quite substantial numbers of copies of the plasmid were present in the cell.

The potential utility of such temperature sensitive runaway mutant plasmids in recombinant methods for securing *E.coli* expression of exogenous gene products was manifest. Because it is often the case that expression of exogenous genes results in formation of products which are toxic or otherwise detrimental to cell metabolism and because yields of exogenous gene products are often diminished by host cell degradation of the foreign polypeptides over a period of time, it was believed that overall yields of desired products could be optimized by delaying replication of recombinant plasmids until host cells had reached their maximum cell culture densities in the fermentor. In this way large scale DNA transcription and mRNA translation required for host expression of a desired adventitious gene could be temporally regulated to occur at a time close to final product harvest, when host cell detriment and product degradation would have minimal effects of overall product yields.

The first of the temperature sensitive runaway mutant plasmids to be isolated, however, suffered numerous drawbacks which made them unattractive as potential expression vectors for use in securing large scale microbial synthesis of commercially significant proteins. First of all, the plasmids were quite large (averaging around 10 to 12 Kb in size) and their runaway replication in host cells thus constituted a substantial energy drain. This difficulty was alleviated in part upon the development of smaller sized, "mini-plasmids" such as the 4.6 Kb pKN402 (Deutsche Sammlug von Microorganismen, "DSM" Accession No. 1228) but was exacerbated even for the mini plasmids upon insertion of one or more "marker" genes coding for a protein product indicative of plasmid maintenance in the host (e.g., a gene for coding for β-lactamase production resulting in transformed host cell phenotypic resistance to ampicillin). Plasmid pKN402-derived plasmids including marker genes include, e.g., the ampicillin-resistance conferring plasmid pKN403 (DSM Accession No. 1229), plasmid pKN404 conferring streptomycin resistance, and plasmids pMOB45 and pMOB48 [10.5 Kb and 9.5 Kb, respectively, see Bittner, et al., *Gene*, 15, pp. 318–329 (1981)] which confer chloramphenicol and/or tetracycline resistance. With the insertion of even a moderately-sized exogenous gene with a functionally associated promoter/regulator sequence the plasmid size could easily extend to 11 or 12 Kb. Large plasmid size and attendant host cellular energy drains upon runaway replication result in significant problems in view of the relatively high "basal" copy numbers and the enormously high "runaway" copy numbers for a pKN402 and many of its derivatives. U.K Patent 1,557,774, for example, reports 50 plasmid copies per cell (a "copy number" of 25) for pKN402-tranformed *E.coli* at 30° C. and amplification up to about 5000 plasmid copies per cell upon shift in cell culture temperature to 40°. While such high copy numbers are advantageous in the sense of favoring extensive mRNA transcription of exogenous genes, much of the total cellular energy is wasted in DNA replication and mRNA transcription of DNA sequences having little, if any, consequence to the goal of exogenous gene expression. Depletion of cellular energy resources, of course, has a direct and unfavorable influence on the rate of mRNA translation into desired protein products.

The problems associated with relatively high basal copy numbers of common temperature sensitive runaway mutant plasmids take on even greater significance upon consideration of potential exogenous gene product toxicity because even at low ("permissive") temperatures the high rates of transcription and translation events can provide quantities of gene product which interfere with optimal host cell growth in culture. Manipulations geared toward reducing the basal and amplified (elevated temperature induced) copy number of runaway mutant plasmids have generally resulted in either loss of temperature sensitivity characteristics or loss of the capacity for maintenance of the plasmids in host cells. See, e.g., Hashimoto-Gotoh, et al., *Gene*, 16, pp. 227–235 (1981). Of interest to the background of the present invention is the independent notation of the existence of "partition" DNA sequences in pSC101-derived plasmids, which sequences reportedly facilitate stable plasmid inheritance. See, Meacock, et al., *Cell*, 20, pp. 529–542 (1980).

A partial attempt to deal with the problem of toxic gene product "leakage" occasioned by high basal copy numbers has taken the form of incorporation of structural gene transcription promoter DNA sequences functionally associated with "strong" repressor (operator) sequences which allow for highly selective chemical or, preferably, thermal control of exogenous gene expression. See, e.g., Sninsky, et al., U.S. Letters Patent No. 4,374,927; Sninsky, et al., *Gene*, 16, pp. 275–286 (1981); Remaut, et al., *Gene*, 22, pp. 103–113 (1983).

The use of "strong" promoter sequences in pKN402-derived plasmids, of course, occasions corresponding potential losses in overall efficiency of gene expression owing to the lack of correspondingly strong mRNA transcription termination sequences. In the absence of such sequences, mRNA transcription of exogenous genes will ordinarily be accompanied by a "read through" into adjacent DNA sequences with corresponding cellular energy drains, possible significant interference with exogenous gene mRNA binding to ribosomes (owing to "oversizing") and, in the case of the temperature sensitive runaway mutants, possible interference with proper transcription of DNA sequences essential to autonomous replication of the plasmid and the runaway characteristic.

Another disadvantage of pKN402-derived plasmids has been the general lack of unique restriction endonuclease enzyme recognition sites which would allow ready incorporation of exogenous gene sequences. Where present, such unique sites are frequently at positions intermediate a marker gene, effectively necessitating plasmid constructions involving two selectable phenotypic marker genes to allow for both exogenous gene insertion and verification of host transformation. See, Hashimoto-Gotoh, et al., supra, but cf, Remaut, et al., supra, discussing insertion of a "mutlilinker sequence" in a 7 Kb pKN402-derived plasmid designated pCP3.

Despite substantial efforts at modification of the originally isolated runaway mutants, there continues to exist a need in the art for small-sized, autonomously-replicating, stably-maintained, selectable, circular DNA plasmids having temperature sensitive copy number mutant replication characteristics. Optimal plasmids of this description would have relatively low basal copy numbers (in the range of 1 to 20 and preferably 1 to 10) as well as relatively low amplified, temperature elevation-induced, copy numbers (in the range of 100 to an unlimited number and preferably 100 to 300) and would thereby avoid both excessive cellular energy drains during maintenance and runaway condition induction and premature "leakage" of exogenous gene products into transformed host cytoplasm. Optimal plasmids would include DNA sequences operative to provide for ready incorporation of exogenous genes without interfering with the function of selectable marker genes and would also provide DNA sequences operates as mRNA transcription terminators. The latter DNA sequences would be provided at a locus wherein they could function to terminate transcription of inserted exogenous genes, especially those under the control of strong promoter DNA sequences which might optionally be provided in such optimal plasmids.

BRIEF SUMMARY

The present invention provides novel circular DNA plasmids exceptionally useful as vectors in recombinant methods for securing high levels of expression of exogenous genes.

Plasmids of the invention generally comprise discrete DNA sequences operative to: (1) confer upon the plasmid the capacity for autonomous replication in a host cell; (2) control autonomous plasmid replication in relation to the temperature at which host cell cultures are maintained; (3) stabilize maintenance of plasmid in host cell populations; (4) direct synthesis of a protein product indicative of plasmid maintenance in a host cell population; (5) provide, in sequence, a plurality of restriction endonuclease recognition sites, unique to the plasmid and facilitative of exogenous gene DNA sequence insertion; and (6) terminate mRNA transcription of exogenous gene sequences inserted within the plasmid at said unique restriction endonuclease restriction sites.

Plasmids of the invention preferably have a size of less than 5.0 kilobases (exclusive of any inserted exogenous gene), have relatively low basal copy numbers and optionally include a DNA sequence operative to provide a strong promoter of mRNA transcription which is functionally associated with a temperature sensitive respressor sequence. Presently preferred embodiments of novel plasmids of the invention include plasmid pCFM414, which was deposited with the American Type Culture Collection, 12301 Parklawn Drive, Rockville, Md., on Jul. 21, 1983 in accordance with the U.S. Patent and Trademark Office's requirements for microorganism deposits, and designated A.T.C.C. No. 40076; plasmids pCFM424, pCFM510, pCFM511, pCFM512, pCFM516, pCFM517, pCFM526, pCFM536, pCFM636, pCFM736, and pCFM836, whose construction are disclosed in detail herein for duplication by those skilled in the art. In transformed *E.coli* cells, a basal copy number of about 20 or less is maintained for these plasmids at temperatures below 34° C.

Plasmids of the invention provide for high level *E.coli* expression of exogenous structural genes as exemplified by genes coding for such diverse polypeptides as human insulin-like growth factor, human urogastrone and the alpha subunit of bovine glycoprotein hormone. Numerous other aspects and advantages of the present invention will become apparent to those skilled in the art upon consideration of the following detailed description thereof.

DETAILED DESCRIPTION

The present invention provides a class of circular DNA plasmid vectors which possess the substantive advantages of temperature sensitive copy number mutant plasmids currently available in the art but which are substantially free of many of the functional defects of such plasmids. Plasmids of the invention further possess characteristics not presently available in temperature-sensitive runaway plasmids which render them exceptionally suitable for use in securing *E.coli* expression of exogenous gene products. Plasmids constructed according to the invention generally comprise a novel combination of physically discrete (non-overlapping), functionally cooperative DNA sequences.

1. Each plasmid of the invention incorporates a DNA sequence operative to confer upon the plasmid the capacity for autonomous replication in host *E.coli* cells. Specifically suitable for use in achieving this function are DNA sequences comprising (1) the gene commonly referred to as "Rep A" and (2) an "origin of replication" ("ori") sequence. The Rep A gene codes for *E.coli* synthesis of an approximately 33,000 dalton protein whose concentration in *E.coli* is thought to directly determine the number of plasmid replication initiation events. See, e.g., Kollek, et al., *Mol.Gen.Genet.*, 162, pp. 51–57 (1978) and Light, et al., *E.M.B.O. Journal*, 2, pp. 93–98 (1983). The "ori" sequence includes a sequence coding for "Rep A4", a 14,000 dalton protein.

2. Each plasmid of the invention incorporates a DNA sequence operative to confer thermal sensitive control of plasmid copy number. By way of example, a suitable copy number control sequence would include (1) a gene coding for "cop B", and (2) a "cop A" sequence. The cop B gene codes for *E.coli* production of an approximately 11,000 dalton protein which operates as a transacting repressor. Cop B is made constitutively in the cell depending on cell growth conditions and functions as a repressor by binding to a region at or near the promoter for transcription of Rep A. Cop A is a 90 nucleotide RNA-synthesis-directing sequence. Transcribed RNA is made in the opposite orientation to transcription of Rep A protein and the cop A overlaps the leader mRNA directing sequence which precedes the Rep A sequence. Cop A RNA apparently operates by way of an RNA-RNA interaction that decreases translation of the Rep A protein. See, e.g., Stougaard, et al., *Proc.Nat'l.Acad.Sci. U.S.A.*, 78, pp. 6008–6012 (1981); Molin, et al., *Mol.Gen. Genet.*, 181 pp. 123–130 (1981); Light, et al., *J.Bacteriol.*, 151, pp. 1129–1135 (1982); Light, et al., *E.M.B.O. Journal*, 2, pp. 93–98 (1983).

3. Each plasmid of the invention incorporates a DNA sequence participative in maintenance of the plasmid in host cells. Typically derived from a stable low copy number *E.coli* plasmid and referred to as the par locus within the plasmid, such sequences operate to ensure that during host cell division at least one copy of each plasmid present in the parent cells will be distributed to daughter cells. See, e.g., Meacock, et al., *Cell*, 20, pp. 529–542 (1980).

4. Each plasmid of the invention incorporates a DNA sequence operative to generate a protein "marker" substance which indicates plasmid maintenance in host cells. Typically, such a sequence codes for a protein conferring antibiotic resistance.

5. Each plasmid of the invention incorporates a DNA sequence providing at least two and preferably three or more recognition sites for restriction endonuclease cleavage which are unique to the plasmid (i.e., not present in any other region of the plasmid) and hence permit ready insertion of an exogenous gene.

6. Each plasmid of the invention incorporates a DNA sequence operative as a terminator of mRNA transcription of adjacent DNA sequences and situated within the plasmid so as to terminate transcription of an exogenous gene inserted within the plasmid. While typically derived from 3' untranslated regions of viral genomic DNA, such sequences might simply comprise a series of multiple translation a stop codons which appear to function as mRNA transcription terminators in some instances. See, e.g., Gentz, et al., *Proc. Nat'l.Acad.Sci.U.S.A.*, 78, pp. 4936–4940 (1981) and Yanofsky, *Nature*, 289, pp. 751–758 (1981).

All the above discrete functional DNA sequences of plasmids of the invention are preferably provided with a minumum of intervening non-functional DNA sequences so that the size of the plasmid may be 5 Kb or less, allowing for optimal efficiency in the management of host cellular energy resources. Preferred plasmids of the invention may also include a DNA sequence operative as a promoter of mRNA transcription functionally associated with a plasmid-borne or host chromosomal DNA sequence operative to control the promoter. Promoter function could be thermally dependent in the same manner as plasmid copy control, e.g., a thermal stimulus which would serve to diminish repression of plasmid replication would serve to derepress the promoter. Optimally, enhanced plasmid replications would occur at a first elevated temperature and derepression of the promoter would occur at a second, higher, elevated temperature. Such a promoter/regulator DNA sequence could be situated within plasmids of the invention at a locus adjacent the transcription termination sequence and spaced apart therefrom by the above-noted gene-insertion-facilitating series of unique restriction sites. Alternatively, the regulator sequence could be located on a separate plasmid or carried on host cell chromosomes.

The following examples serve to illustrate construction and use of plasmids of the invention. More particularly, Example 1 relates to construction and characteristics of plasmid pCFM414 according to the invention; Examples 2 through 4 respectively relate to use of pCFM414 to achieve high levels of *E.coli* expression of genes for human insulin-like growth factors human urogastrone and a bovine glyco-protein hormone subunit; Examples 5 through 7 relate to construction and characteristics of alternative temperature sensitive plasmids according to the invention.

EXAMPLE 1

Plasmid pCFM414 consists of approximately 4465 base pairs and includes a single EcoRI restriction site, the 3' terminal base pair (C/G) of which is designated base pair number 1 of the plasmid. (Unless otherwise indicated, base pair numbers used in conjunction with restriction sites will indicate the 3'-most initial pair of residues remaining upon cleavage with the designated enzyme.) Set out in Table I below is the sequence of base pairs 1 through 36 of pCFM414.

TABLE I

| EcoRI | HpaI | XbaI | NcoI | HindIII | XhoI | BamHI |
|---|---|---|---|---|---|---|
| 1 | | | | | | 36 |

GAATTCGTTAACTCTAGACCATGGAAGCTTACTCGAGGATC
CTTAAGCAATTGAGATCTGGTACCTTCGAATGAGCTCCTAG

The Table I sequence is seen to comprise a sequence of base pairs providing a series of recognition sites for cleavage by restriction endonuclease enzymes HpaI, XbaI, NcoI, HindIII, XhoI, and BamHI, all of which are unique to pCFM414. (While the manufactured Table I sequence was designed to include an XbaI recognition site, attempts to cut pCFM414 with the enzyme have not been uniformly successful.

Commencing with bp 37 and extending through bp 235 is a transcription terminator sequence. More specifically, the sequence comprises the "Toop" terminator of lambda bacteriophage obtained from plasmid pKO1-T [See, McKenney, et al., *Gene Amplif.Anal.*, 2, pp. 383–415 (1981)] on a MboI fragment to which were added "linker" bases providing a 199 bp fragment with BamHI sticky ends. In the process of incorporation into pCFM414, the "rightward" BamHI site of the Toop-containing fragment was not reconstituted and thus the uniqueness of the "leftward" BamHI site within the final plasmid construction was preserved.

The DNA sequence spanning bp 236 through 415 of pCFM414 is a residue of intermediate construction procedures employed in developing the final plasmid. The DNA had its origins in plasmid pSM2 [See, Mickel et al., *J.Bacteriol.*, 127, pp. 644–655 (1976)] as a BclI to BglII fragment. In the course of pCFM414 construction, the BclI site was lost upon ligation to the BamHI ended fragment (providing bp 37–235) as described in the preceding paragraph. The entire transcription terminator sequence (bp 37–235 and bp 236–415 may be excised from pCFM414 by BamHI and BglII digestion.

The DNA sequence of pCFM414 spanning bp 416 through 1259 was derived from pKN402 as a partial BglII and SalI digestion product. The sequence includes an *E.coli* cop B gene and its promoter, the cop A sequence and a portion of the initial sequence of the Rep A gene. The sequence may be removed from pCFM414 by a partial BglII and SalI digestion.

The pCFM414 sequence spanning bp 1260 through 2879 was derived as partial PstI and SalI digestion fragment of plasmid NR1 (R100) [See, Rownd, et al., *Ann.N.Y.Acad.Sci.*, 182, pp. 188–206 (1971)]. The PstI site was blunted off and a synthetic SstI linker was added. The sequence includes codons for synthesis of Rep A and also includes an "ori" sequence incorporating the Rep A4 gene. The sequence including bp 1260–2879 may be excised from pCFM414 by SalI and SstI digestion.

Spanning bp 2880 through 4088 of pCFM414 is a gene coding for *E.coli* production of β-lactamase enzyme which confers an ampicillin resistant phenotype. The sequence was originally derived as an EcoRI and partial HgaI digestion fragment of pBR322. Subsequently an internal sequence of this gene (spanning XmnI and BglI restriction sites) was replaced by a XmnI to BglI digestion fragment from the β-lactamase gene of plasmid pUC9 [Vieira, et al., *Gene*, 19, pp. 259–268 (1982)] which does not provide either a HincII or a PstI restriction site.

Base pairs 4089 through 4462 of pCFM414 comprise a partition regulation sequence derived from pSC101 (A.T.C.C. 37032) as a HincII and AvaI digestion fragment. Digestion of pCFM414 with EcoRI and SstI will yield a single fragment comprising base pairs 4089 through 4462.

Table II, below, provides in tabular form a summary of pCFM414 constituents. Restriction endonuclease recognition site designations appearing in brackets are indicative of those sites associated with the derivation of particular fragments which were destroyed by blunt-ending prior to plasmid construction or "lost" in the course of joining with a sticky and that did not restore the complete restriction site.

TABLE II

| Sequence | Principal Function |
| --- | --- |
| Base Pairs 0–36 EcoRI — BamHI | Restriction sites for gene insertion |
| Base Pairs 37–235 [MboI] — [MboI] BamHI — [BamHI] | mRNA transcription termination |
| Base Pairs 236–415 [BclI] — BglII | "Spacer" and possible mRNA transcription termination |
| Base Pairs 416–1259 BglII — SalI | Cop A and Cop B gene |
| Base Pairs 1260–2879 SalI — SstI | Rep A gene and "ori" including Rep A4 gene |
| Base Pairs 2880–4088 [HgaI] — [EcoRI] SstI — [EcoRI] | β-lactamase gene |
| Base Pairs 4089–4462 AvaI — [HincII] AvaI — EcoRI | Stability sequence |

While the incorporation of the above-noted specific sequences allowed for construction of pCFM414 in a size of less than 4.5 kilobases, it will be apparent that alternative DNA sequences providing identical functional characteristics could be incorporated into plasmids of the invention although use of available alternative sequences appears unlikely to be as DNA "conservative".

Transcription termination sequences other than "Toop" derived from lambda bacteriophage may be suitably selected from among those described, for example, in Adhya, et al., *Ann.Rev.Biochem.*, 47, pp. 967–996 (1978). For descriptions of sources of DNA sequences providing the stabilizing or partition maintenance function other than the "par" locus of pSC101, see, Som, et al., *Plasmid*, 5, pp. 150 et seq. (1981), Nordstrom, et al., *Plasmid*, 4, pp. 215 et seq. (1980) and McKell, et al., (Abstract) page 347, J. Supramolecular Structure Supp. No. 4, 9th Annual ICN-UCLA Symposium (1980). Alternative sources of "ori" and RepA4 gene sequences operative to confer autonomous replication of plasmids of the invention include those described in Rosen, et al., *Mol.Gen.Genet.*, 179, pp. 527–537 (1981). Plasmid NR1 can provide an alternative source of a CopA DNA sequence as well as a CopB gene. See, Stougaard, et al., *Mol.Gen.Genet.*, 181, pp. 116–122 (1981).

Upon transformation of *E.coli* cells (e.g., K-12 strains AM7, JM103 or the like), the copy number of pCFM414 within cells maintained at below 34° C. (i.e., at 30° C.) is 20. Elevation of culture temperature to above 34° C. (i.e., to 37° C.) results in uncontrolled replication until cell death occurs. On the whole, elevation of culture temperature from 30° C. to 37° C. will give rise to a doubling in copy number about every fifteen minutes. Elevation from 30° C. to 42° C. results in copy number doubling about every twelve minutes.

The following example relates to use of pCFM414 to secure *E.coli* expression of a gene coding for the alpha subunit of bovine glycoprotein hormone.

EXAMPLE 2

Two plasmids were constructed for use in securing direct *E.coli* expression of the alpha subunit common to bovine glycoprotein hormones, and were utilized to examine the effect of pCFM414 on expression of an exemplary gene. A first plasmid, pBα-E$_2$, contained a cDNA-derived structural gene for the alpha subunit polypeptide in association with a trp promoter. A second plasmid, pBα-E$_3$, was constructed by incorporation of the entire promoter and structural gene sequence from pBα-E$_2$ into plasmid pCFM414 which had been digested with EcoRI and BamHI.

Growth of *E.coli* AM7 cells transformed with pBα-E$_2$ resulted in production of approximately 2.5 mg/OD-liter of the desired polypeptide. *E.coli* AM7 cells transformed with pBα-E$_3$ were initially grown at 28° C. and the culture temperature was then raised to 37° C. Production of the desired polypeptide by the pBα-E$_3$ transformed AM7 cells was estimated by gel chromatography to be approximately 25 mg/OD-liter, or approximately ten-fold the production of pBα-E$_2$ transformed AM7 cells.

The following example relates to use of pCFM414 to secure *E.coli* expression of a gene coding for the alpha subunit of human urogastrone.

EXAMPLE 3

This example summarizes experimental data set out in co-owned, co-pending U.S. application Ser. No. 486,091, [PCT International Publication No. WO83/04030, published Nov. 24, 1983] entitled "The Manufacture and Expression of Genes for Urogastrone and Polypeptide Analogs Thereof", filed Apr. 25, 1983 by Banks, et al. Briefly put, two significant plasmids were constructed for use in securing direct *E.coli* expression of human urogastrone. A first plasmid, pADH-25, contained a manufactured structural gene for urogastrone in association with a trp promoter. A second plasmid, pADH-59, was constructed by incorporation of the entire promoter and structural gene sequence from pADH-25 into pCFM414 which had been digested with EcoRI and KhoI.

Growth of *E.coli* JM103 cells transformed with pADH-25 resulted in production of approximately 15 micrograms/OD-liter of the desired polypeptide by radioreceptor assay. *E.coli* JM103 cells transformed with pADH-59 were initially grown at about 30° C. and the culture temperature was then raised to 37° C. Production of the desired polypeptide by the pADH-59 transformed JM103 cells was estimated by gel chromatography to be approximately 50 mg/OD-liter, or well over a hundred-fold increase over the production by pADH-25 transformed JM103 cells.

The following example relates to use of pCFM414 to secure *E.coli* expression of a gene coding for the alpha subunit of human insulin-like growth factor.

EXAMPLE 4

This example summarizes experimental data set out in co-owned, co-pending, concurrently-filled U.S. application Ser. No. 521,966, entitled "Microbial Expression of Insulin-Like Growth Factor", filed Aug. 10, 1983, and its Continuation-in-part U.S. Ser. No. 633,451, filed Jul. 26, 1984, by Banks, et al. Briefly put, two significant plasmids were constructed for use in securing direct E.coli expression of insulin-like growth factor. A first plasmid, pT5-4-IGF-I, contained a manufactured structural gene for the polypeptide in association with a synthetic promoter. A second plasmid, pADP-223, was constructed by incorporation of the entire promoter and structural gene sequence of pT5-4-IGF-I into pCFM414 which had been digested with HindIII and XhoI.

Growth of E.coli JM103 cells transformed with pT5-4-IGF-I resulted in production of approximately 2 micrograms per OD-liter of the desired polypeptide. E.coli JM103 cells transformed with pADF-223 were initially grown at 28° C. and the culture temperature was then raised to 37° C. Production of the desired polypeptide by the pADF-223 transformed JM103 cells was estimated by gel chromatography to be approximately 5 micrograms per OD-liter, or approximately two-fold the production of pT5-4-IGF-I transformed JM103 cells.

The following examples relates to alternative construction for a plasmid according to the present invention.

EXAMPLE 5

A first series of plasmids was constructed based on pCFM414 and principally involving alterations in the copy control regions. These were designated pCFM510, pCFM511, pCFM512, pCFM516 and pCFM517 and their preparation is set out below.

A. pCFM510

Plasmid pCFM414 was digested with BglII and PstI to delete the (pKN402-derived) Cop A and Cop B regions and the large fragment was retained. Plasmid NR1 was digested with BglII and PSTI and the small fragment containing the NR1 Cop A and Cop B sequences was isolated and ligated into the large fragment of pCFM414 to provide pCFM510. The plasmid therefore principally comprises the entire Cop A, and Cop B, "Rep A" and "ori" sequences of NR1 and has six more base pairs (4471) than pCFM414 (4465).

B. pCFM511

Plasmid pCFM414 was digested with BglII and PstI to delete the (pKN402-derived) Cop A and Cop B regions and the large fragment was retained. Plasmid pSM1, a derivative of pR12 [see, Stougaard, et al., *Molec.Gen.Genet.*, 181, pp. 116–112 (1981) and Rosen, et al., *Molec.Gen. Genet.*, 179, pp. 527–537 (1980)] was digested with BglII and PstI and the small fragment containing the pSM1 Cop A and Cop B sequences was isolated and ligated into the large fragment of pCFM414 to provide pCFM511. The plasmid therefore principally comprises the Cop A and Cop B sequences of pSM1 and the "Rep A" and "ori" sequences of NR1 and has six more base pairs (4468) than pCFM414 (4462).

C. pCFM512

Plasmid pCFM414 was partially digested with XmnI and PstI to delete the (pKN402-derived) Cop A sequence of pCFM414 and the large fragment was retained. Plasmid NR1 was digested with XmnI and PstI and the small fragment containing the Cop A sequence was isolated and ligated into the large fragment of pCFM414 to provide pCFM512. During the construction, the XmnI restriction site was destroyed as a result of a two base pair deletion. The plasmid therefore principally consisted of the Cop A region of NR1, the Cop B region of Beu 1, and the "Rep A" and "ori" sequences of NR1 and has a size of 4460 base pairs.

The promoter that transcribes the Cop B mRNA has a single base pair mutation (at 435) which is T/A rather than C/G. This mutation is responsible for the temperature sensitive copy number phenotype.

D. pCFM516 and pCFM517

Plasmid pCFM512 as prepared in part (C) above was subjected to hydroxylamine mutagenesis in order to alter a single base pair (598) in the Cop B protein coding region from C/G to T/A. Plasmid pCFM516 contained this single base pair mutation (effectively changing the amino acid coded for from alanine to valine). Plasmid pCFM517 contained at least one as-yet undetermined base pair mutation in the region between 848 and 1282.

EXAMPLE 6

Plasmids pCFM414 of Example 1 and plasmids pCFM510, pCFM511, pCFM512, pCFM516 and pCFM517 of Example 5 were screened for plasmid copy number characteristics in exponential and stationary phases of host cell growth as well as for protein product expression.

A protein αCon-1-IFN coding for production of a consensus leucocyte interferon polypeptide was employed as the "model" sequence for insertion into the plasmids. The αCon-1-IFN sequence with its preceding Shine-Delgarno sequence optimized for translation initiation and with a lambda bacteriophage promoter was inserted into each EcoRI/BamHI digested plasmid.

Each plasmid was co-transformed into an E.coli FM3 host with another pSC101-derived plasmid into which had been cloned a 1.1 Kb (BglII to PstI) lambda bacterio-phage DNA fragment including the gene coding for the PL repressor protein, CI857. At 42° C., the CI857 protein is inactivated, inducing the PL promoter to initiate transcription.

From fresh overnight cultures in L Broth+50 ug/ml Ampicillin each plasmid-host system was inoculated into L Broth and grown at 28° C. to mid exponential optical density. (_1.0 OD$_{600nm}$ Beckman Spectrophotometer). Cell aliquots (2.0 ODml) were taken for copy number and protein gel analysis. The cultures were diluted to low cell densities in L Broth and allowed to grow at 42° C. for up to 4 hours. Cell aliquots (2 ODml) were again taken for copy number and protein gel analysis.

Table III below provides a summary of relative plasmid copy number/host genome equivalent at different growth temperatures. Plasmid copy number is roughly calculated by isolating (alkaline lysate procedure) plasmid DNA from 2 ODml of cell pellet and comparing the amount of DNA/ODml to a standard plasmid with known copy number (pCFM511, copy No. =20).

TABLE III

Relative Plasmid Copy Number

| Plasmid | Stationary Phase at 28° C. | Exponential Phase | | |
|---|---|---|---|---|
| | | at 28° C. | at 37° C. | at 42° C. | at 42° C.* |
| pCFM414 | 200 | 20 | runaway | runaway | 50 |
| pCFM510 | 4 | 2 | 2 | 2 | 2 |
| pCFM511 | 40 | 20 | 20 | 20 | 10 |
| pCFM512 | 4 | 2 | 10–20 | 50–100 | — |
| pCFM516 | 20 | 10 | 100–200 | runaway | 100 |
| pCFM517 | 40 | 20 | 200–400 | runaway | 100 |

*With P$_L$-αCon-1-IFN gene insert

The right-hand column of Table III illustrates the variation in plasmid copy number obtained when host cells were transformed with the plasmids containing the αCon-1-IFN sequence. Analysis of the protein products of the host cells revealed that the desired polypeptide constituted 14–17% of the total cell protein of the pCFM510 transformed cells; 25–30% of the pCFM511 transformed cells; and 60–70% of the pCFM414, pCFM516, and pCFM517 transformed cells.

EXAMPLE 7

Certain additional plasmids of the invention were desired for the purposes of (a) increasing the number of unique restriction sites present in pCFM414; and/or (b) incorporating a promoter sequence into the vector with and without a ribosomal loading sequence; and/or (c) changing the ampicillin resistance, β-lactamase marker gene in pCFM414 to another antibiotic resistance marker gene. The newly designed plasmids are designated pCFM424, pCFM526, pCFM536, pCFM636, pCFM736 and pCFM836, the preparation of which is as follows:

A. pCFM424

A derivative of plasmid pCFM414, designated pCFM424, consists of approximately 4622 base pairs and includes the following:

(1) the entirety of the pCFM414 sequence extending from base pairs 37 through 4462;

(2) a lambda bacteriophage $P_L$ promoter; and (3) an expanded "bank" of restriction endonuclease enzyme recognition sites as well as an adjacent sequence of base pairs providing multiple "stop" codons.

More specifically, the sequence of 196 base pairs set out in Table IV below replaces the sequence of base pairs occupying positions 1–36 of pCFM414.

gene could be isolated from lambda bacteriophage DNA as a 1.1 Kb PstI to BglII fragment. This could be inserted into a suitable low copy plasmid which could be "cotransformed" into a suitable host with a pCPM424. The fragment could also be associated within a translocation sequence and integrated into the chromosome of any selected host E.coli strain.

It is expected that plasmid pCFM424 will permit thermally-inducible expression of selected exogenous genes and that its use will provide quantities of desired polypeptide products in excess even of those provided by pCFM414.

B. pCFM526

Plasmid pCFM 526 is prepared as a derivative pCFM516 and differs from it in terms of deletion of the restriction site bank sequence spanning base pairs 1 through 36 and insertion of a sequence of 220 base pairs set out in Table V.

TABLE IV

```
1
5'-CCGGATCTCTCACCTACCAAACAATGCCCCCCTGCAAAAAATAAATTCATATAAA
3'-GGCCTAGAGAGTGGATGGTTTGTTACGGGGGGACGTTTTTTATTTAAGTATATTT

AAACATACAGATAACCATCTGCGGTGATAAATTATCTCTGGCGGTGTTGACATAAA
TTTGTATGTCTATTGGTAGACGCCACTATTTAATAGTGACCGCCACAACTGTATTT

HgiA   ClaI  HpaI   XbaI  NcoI  HindIII  XhoI  BamHI  SstII
TACCACTGGCGGTGATACTGAGCACATCGATGTTAACTCTAGACCATGGAAGCTTACTCGAGGATCCGCGGATAA
ATGGTGACCGCCACTATGACTCGTGTAGCTACAATTGAGATCTGGTACCTTCGAATGAGCTCCTAGGCGCCTATT

195
ATAAGTAACGATC
TATTCATTGCTAG
```

The Table IV sequence is seen to comprise a sequence of base pairs providing a series of recognition sites for cleavage by restriction endonuclease enzymes HgiA, ClaI, HpaI, XbaI, NcoI, HindIII, XhoI, BamHI, and SstII, all of which are unique to pCFM424.

Furthermore, a lambda $P_L$ promoter sequence derived from plasmid pKC30 [See, e.g., Shimatake, et al., *Nature*, 292, pp. 128–132 (1981)] as a 130 base pair fragment by digestion with BglII and HglA is present in pCFM424 at a locus following the stability gene sequence and preceding the restriction site "bank".

Control over the $P_L$ promoter within a pCFM424-transformed host may be provided in a number of ways through use of the $C_{I857}$ repressor gene. As one example, E.coli strain K12ΔHtrp has this gene integrated into the bacterial chromosome and could provide the host. See, Bernard, et al., *Gene*, 5, pp. 59–76 (1979). Alternatively, the

TABLE V

```
1
5'-CCGGATCTCTCACCTACCAAACAATGCCCCCCTGCAAAAAATAAATTCATATAAA
3'-GGCCTAGAGAGTGGATGGTTTGTTACGGGGGGACGTTTTTTATTTAAGTATATTT

AAACATACAGATAACCATCTGCGGTGATAAATTATCTCTGGCGGTGTTGACATAAA
TTTGTATGTCTATTGGTAGACGCCACTATTTAATAGTGACCGCCACAACTGTATTT

HgiA    ClaI
TACCACTGGCGGTGATACTGAGCACATCGATAAAACCATGAGGGTAATAAATAATG
ATGGTGACCGCCACTATGACTCGTGTAGCTATTTTGGTACTCCCCATTATTATTAC

XbaI   EcoRI  HpaI  KpnI  NcoI  HindIII  XhoI  BamHI
ATGAAGGAGACTATCTAGAATTCGTTAACGGTACCATGGAAGCTTACTCGAGGATC
TACTTCCTCTGATAGATCTTAAGCAATTGCCATGGTACCTTCGAATGAGCTCCTAG
```

The design for pCFM526 is thus seen to include the $P_L$ promoter, an expanded bank of unique restriction sites (vis-a-vis pCFM414) and a ribosomal loader sequence intermediate the promoter and the major components of the restriction bank.

C. pCFM536

Plasmid pCFM536 is also prepared as a derivative of pCFM516 and differs from it in terms of deletion of the restriction site bank sequence spanning base pairs 1–36 and insertion of a sequence of 188 base pairs set out in Table VI.

tion of a SstI linker to the SmaI sticky end an NdeI linker to the HindIII sticky end. The "par" locus sequence may be obtained, as in Example I, as a HincII to AvaI digestion fragment of pSC101. For combination with the Kanamycin gene and insertion into the large fragment of pCFM536, the HincII end is first treated with a SalI linker and then an AatII linker. The AvaI site is treated with a BamHI linker and then an NdeI linker. The large fragment of pCFM536 (AatII/SstI), the Kanamycin gene fragment (SstI/NdeI) and the par locus fragment (AstII/NdeI) are mixed and ligated to form pCFM636.

TABLE VI

```
1
5'-CCGGATCTCTCACCTACCAAACAATGCCCCCCTGCAAAAAATAAATTCATATAAA
3'-GGCCTAGAGAGTGGATGGTTTGTTACGGGGGGACGTTTTTTATTTAAGTATATTT

AAACATACAGATAACCATCTGCGGTGATAAATTATCTCTGGCGGTGTTGACATAAA
TTTGTATGTCTATTGGTAGACGCCACTATTTAATAGTGACCGCCACAACTGTATTT

HgiA    ClaI  HpaI
TACCACTGGCGGTGATACTGAGCACATCGATGTTAAC
ATGGTGACCGCCACTATGACTCGTGTAGCTACAATTG

XbaI  EcoRI  HpaI  KpnI  NcoI  HindIII  XhoI  BamHI
TCTAGAATTCGTTAACGGTACCATGGAAGCTTACTCGAGGATC
AGATCTTAAGCAATTGCCATGGTACCTTCGAATGAGCTCCTAG
```

The design for pCFM 536 is thus seen to be similar to that of pCFM526 except for the absence of the ribosomal loader sequence.

D. pCFM636

Plasmid pCFM636 is prepared as a derivative of pCFM536, constructed to incorporate a Kanamycin resistance marker gene in place of the ampicillin resistance marker. The β-lactamase gene is first deleted by digestion of pCFM536 with SstI and EcoRI (partial, at EcoRI site preceding the $P_L$ promoter) and the EcoRI site is converted to an AatII site by a linker which "kills" the EcoRI site by omission of the initial G/C base pair. This serves to delete not only the marker gene but also the entire "par" or stability sequence. The Kanamycin gene sequence may be obtained as a SmaI to HindIII fragment from the Tn5 plasmid of Beck, et al., *Gene*, 19, pp. 327–336 (1982) or Auerswald, et al., *Cold Spring Harbor Symp. Quant. Biol.*, 45, pp. 107–113 (1981) and prepared for insertion into the large fragment of the above-noted SstI/EcoRI digestion of pCFM536 by addi- E. pCFM736

Plasmid pCFM736 is prepared as a derivative of pCFM636 and includes a foreshortened $P_L$ promoter sequence. The plasmid is prepared by digestion of pCFM636 with AatII and XbaI and insertion of the following AatII to XbaI fragment:

```
  AatII                                                                    ClaI   XbaI
5'-    CAGATCCATAAATTATCTCTGGCGGTGTTGACATAAATACCACTGGCGGTGATAATGAGCACATCGATT-3'
3'-TGCAGTCTAGGTATTTAATAGAGACCGCCACAACTGTATTTATGGTGACCGCCACTATTACTCGTGTAGCTAAGATC-5'
```

Note that this procedure deletes the second HpaI site present in pCFM636.

F. pCFM836

Plasmid pCFM836 is constructed as a derivative of pCFM736 for the purpose of adding as SstII restriction site to the restriction site bank, adding three nonsense or "stop" codons and "killing" an NcoI site present in the Kanamycin resistance gene. The plasmid may be prepared by digesting pCFM736 with BamHI and inserting the following fragment:

Destruction of the NcoI site in the Kanamycin resistance gene is accomplished by the site specific mutagenesis at the codon for a threonine residue 76 amino acids upstream of the carboxy terminal leucine specified by the Kanamycin resistance gene, and specifically by altering the ACC codon to an ACT codon.

As was the case with the Example 6 expression systems (wherein the exemplary exogenous gene inserted into the plasmids was accompanied by $P_L$ promoter), expression systems involving those of the above plasmids which are designed to include the $P_L$ promoter or shortened $P_L$ promoter will optimally require association of the $C_{I857}$ gene in the system.

Numerous modifications and variations in the invention as above described are expected to occur to those skilled in the art. Consequently, only such limitations as appear in the appended claims should be placed upon the invention.

What is claimed is:

1. A plasmid for use as a transformation vector in recombinant methods to secure *E. coli* expression of exogenous genes, said plasmid comprising:
   (1) nucleotide sequences operative to confer upon the plasmid the capacity for autonomous replication in a host cell, said nucleotide sequences comprising a rep A gene and an origin of replication sequence;
   (2) cop A and copB sequences operative to limit plasmid replication to a copy number of up to about 100 copies per host genome equivalent when host cells are maintained at one temperature as compared to a basal copy number when host cells are maintained at a different temperature;
   (3) a nucleotide sequence encoding a par locus operative to stabilize maintenance of the plasmid in host cell populations;
   (4) a nucleotide sequence operative to direct synthesis of a protein product conferring antibiotic resistance in a host cell population;
   (5) a discrete series of restriction endonuclease recognition sites unique to the plasmid; and
   (6) a terminator of transcription of exogenous gene sequences.

2. A plasmid for use a as a transformation vector in recombinant methods to secure *E. coli* expression of exogenous genes, said plasmid comprising:
   (1) nucleotide sequences operative to confer upon the plasmid the capacity for autonomous replication in a host cell, said nucleotide sequences comprising a rep A gene and an origin of replication sequence;
   (2) cop A and cop B sequences operative to limit autonomous plasmid replication to a copy number of up to about 100 copies per host genome equivalent when host cells are maintained at one temperature as compared to a basal copy number when host cells are maintained at a different temperature;
   (3) a nucleotide sequence encoding a par locus operative to stabilize maintenance of the plasmid in host cell populations;
   (4) a nucleotide sequence operative to direct synthesis of a protein product conferring antibiotic resistance in a host cell population;
   (5) a terminator of transcription of exogenous gene sequences;
   (6) a promoter of mRNA transcription of exogenous gene sequences; and
   (7) a discrete series of restriction endonuclease recognition sites unique to the plasmid, said series being between said promoter and said terminator and adjacent said promoter and said terminator.

3. The plasmid as recited in claim 2 wherein said promoter of transcription is a lambda $P_L$ promoter.

4. A plasmid for use as a transformation vector in recombinant methods to secure *E. coli* expression of exogenous genes, said plasmid comprising:
   (1) nucleotide sequences operative to confer upon the plasmid the capacity for autonomous replication in a host cell, said nucleotide sequences comprising a repA gene and an origin of replication;
   (2) copA and copB sequences operative to limit autonomous plasmid replication to a copy number of up to about 100 copies per host genome equivalent when host cells are maintained at one temperature as compared to a basal copy number when host cell are maintained at a different temperature;
   (3) a nucleotide sequence encoding a par locus operative to stabilize maintenance of the plasmid in host cell populations;
   (4) a nucleotide sequence operative to direct synthesis of a protein product conferring antibiotic resistance in a host cell population;
   (5) a terminator of transcription of exogenous gene sequences;
   (6) a promoter of mRNA transcription of exogenous gene sequences;
   (7) a discrete series of restriction endonuclease recognition sites unique to the plasmid, said series being between said promoter and said terminator; and
   (8) a thermally responsive repressor sequence functionally associated with said promoter sequence of mRNA transcription.

5. The plasmid as recited in claim 1 wherein said plasmid has fewer than 5,000 base pairs.

* * * * *

UNITED STATES PATENT AND TRADEMARK OFFICE
CERTIFICATE OF CORRECTION

PATENT NO.   : 5,674,746
DATED        : October 7, 1997
INVENTOR(S)  : Charles F. Morris It is certified that error appears in the above-identified patent and that said Letters Patent is hereby corrected as shown below:

On the Title page:
Col. 2, Attorney, Agent, or Firm: Delete "Robert B. Winter; Ron K. Levy; Steven M. Odre" and insert therefor --Marshall, O'Toole, Gerstein, Murray & Borun--.

Col. 3, line 37, change "operates" to --operative--.
Col. 7, line 12, change "regulation" to --regulating--.
Col. 9, line 47, change "116-112" to --116-122--.
Col.10, line 30, change "bacterio-phage" to --bacteriophage--.
Col. 11, line 10, change "desired" to --designed--.
Col. 14, line 25, change "(AstII/NdeI)" to --(AatII/NdeI)--.

Signed and Sealed this

Second Day of June, 1998

Attest:

*Attesting Officer*

BRUCE LEHMAN
*Commissioner of Patents and Trademarks*